United States Patent [19]
Crabb et al.

[11] Patent Number: 5,888,748
[45] Date of Patent: Mar. 30, 1999

[54] METHODS AND ARTICLES OF MANUFACTURE FOR THE DETECTION OF CRYPTOSPORIDIUM OCCYSTS

[75] Inventors: Joseph H. Crabb, Newfield, Me.; Nathan Turner, Newmarket, N.H.

[73] Assignee: ImmuCell Corporation, Portland, Me.

[21] Appl. No.: 502,328

[22] Filed: Jul. 13, 1995

[51] Int. Cl.$^6$ .................................................. G01N 33/53
[52] U.S. Cl. ............................... 435/7.3; 435/4; 435/7.1; 435/7.22; 435/7.3; 435/29; 530/412; 530/417; 530/388.2; 530/388.6
[58] Field of Search ...................... 530/412, 417, 530/388.2, 388.6; 435/4, 7.1, 7.22, 29, 7.3

[56] References Cited

U.S. PATENT DOCUMENTS

| | | | |
|---|---|---|---|
| 4,876,013 | 10/1989 | Shmidt et al. | 210/650 |
| 5,558,989 | 9/1996 | Shah et al. | 435/6 |

FOREIGN PATENT DOCUMENTS

| | | | |
|---|---|---|---|
| 0 277 660 | 10/1988 | European Pat. Off. | B01D 13/00 |
| 2 693 474 | 1/1994 | France | C12Q 1/04 |
| WO 94/04681 | 3/1994 | WIPO | C12N 15/30 |
| WO 95/31726 | 11/1995 | WIPO | G01N 33/543 |

OTHER PUBLICATIONS

Robertson et al Microbiology Europe 2:18–26, 1994.
Ware et al (Abstracts of the 95$^{th}$ Gen. Meeting of American Soc of Micrology, 1995.
BiFulco et al Applied and Environmental Micrology 59:772–776, 1993.
Jiang et al Marine Euorogy Progress Series 80:101–107, 1992.
Whitmore et al Water Science and Technology27: 69–76, 1993.
Siddons et al., Journal of Clinical Pathology, 45:479–482, 1992.
Nieminski et al., Applied and Environmental Microbiology, 61:1714–1719, 1995.
Joseph M. Bifulco et al., "Antibody–Magnetic Method for Selective Concentration of Giardia Iamblia Cysts from Water Samples", Applied and Environmental Microbiology, Mar. 1993, pp. 772–776.
Mark W. LeChevallier et al., "Evaluation of the Immunofluorescence Procedure for Detection of Giardia Cysts and Cryptosporidium Oocysts in Water", Applied and Environmental Microbiology, Feb. 1995, pp. 690–697.
Mark W. LeChevallier et al., "Occurence of Giardia and Crytosporidium spp, in Surface Water Supplies", Applied and Environmetal Microbiology, Sep. 1991, pp. 2610–2616.
G. Vesey et al., "Routine monitoring of Cryptosporidium oocytes in water using flow cytometry", Journal of Applied Bacteriology, 1993, pp. 87–90.
Cora E. Musial, et al., "Detection of Cryptosporidium in Water by Using Polypropylene Cartridge Fliters", Applied and Environmental Microbiology, Apr. 1987, pp. 687–692.
G. Vesey et al., "A new method for the concentration of Cryptosporidium oocysts from water", Journal of Applied Bacteriology, 1993, pp. 82–86.
Abstract, Tsai et al., "Simple method of concentrating enteoviruses and hepatitis A virus from sewage and ocean water for rapid detection by reverse transcriptase–polymerase chain reaction", Appl. Environ. Microbiol. 1993 Oct:59(10):3488–91.
Abstract, Tsai et al., "Detection of poliovirus, hepatitis A virus, and retrovirus from sewagee and ocean water by triplex reverse transcriptase PCR", App. Environ. Microbiol, 1994 Jul.;60(7):2400–7.

(List continued on next page.)

Primary Examiner—James C. Housel
Assistant Examiner—Ginny Allen Portmer
Attorney, Agent, or Firm—Kevin M. Farrell

[57] ABSTRACT

Embodiments of the present invention relate to methods and articles of manufacture for the detection of Giardia cysts and Crytosporidium oocysts.

16 Claims, 1 Drawing Sheet

OTHER PUBLICATIONS

Abstract, Paul et al., "Concentration of viruses and dissolved DNA from aquatic environments by vortex flow filtration", Appl. Environ. Microbiol. 1991 Aug.;57(8):2197–204.

Abstract, Bellhouse et al., "A high efficiency membrane separator for donor plasmapheresis", ASAIO Trans. 1988, Jul–Sep;34(3):747–54.

Abstract, Ohashi et al., "Rotation–induced Taylor vortex enhances filtrate flux in plasma separation", ASAIO Trans 1988, Jul–Sep;34(3):300–7.

5,888,748

METHODS AND ARTICLES OF MANUFACTURE FOR THE DETECTION OF CRYPTOSPORIDIUM OCCYSTS

FIELD OF THE INVENTION

This invention relates to methods and articles of manufacture for the detection of Giardia cysts and Cryptosporidium oocysts in water.

BACKGROUND OF THE INVENTION

Giardia cysts and Cryptosporidium oocysts are protozoan intestinal parasites. As used herein "Giardia" refers to a genus of flagellates that parasitize the small intestine of mammals. One species of Giardia of particular significance, *G. Lamblia*, has eight flagella and a flattened heart-shaped appearance under microscope. The organism attaches itself to the intestinal mucosa by sucking organs.

As used herein, "Cryptosporidium" refers to a genus of coccidian sporozoan, which are opportunistic parasites in mammals. Cryptosporidiosis, in immunocompetent individuals, is self-limiting. In compromised individuals, it may be fatal.

Outbreaks of giardiosis and Cryptosporidiosis are typically caused by contamination of water supplies. These water borne organisms are difficult to detect. Presently, seven Giardia cysts per 100 L of water is considered potable. To evaluate water supplies one must be able to reliably and reproducibly detect such a level of Giardia, at a reasonable cost.

Although no acceptable level has been defined for Cryptosporidium, such definition is expected in the near future. The level of Cryptosporidium oocysts in water supplies, like Giardia, will be a small, limited number.

Present technology does not presently permit the detection of Giardia cysts or Cryptosporidium oocysts from water supplies in a reliable, reproducible manner at a reasonable cost. Giardia and Cryptosporidium are presently detected using cartridge filters for concentrating organisms from large volumes of water, followed by immunofluorescence assay (IFA). This method is time consuming, labor intensive and requires considerable analytical expertise. The method suffers from a low efficiency in recovering cysts and oocysts from the sample and frequently produces questionable results.

The present invention is directed to methods and articles of manufacture for the detection of Giardia cysts and Cryptosporidium oocysts. The methods are less time consuming, less labor intensive and are more reliable in the recovery of Giardia cysts and Cryptosporidium oocysts than previous methods.

SUMMARY OF THE INVENTION

The present invention features methods and articles of manufacture for the detection of Giardia cysts and Cryptosporidium oocysts in samples. One embodiment of the present invention is a method of detecting the presence or absence in a sample of at least one of the organisms selected from the group consisting of Cryptosporidium and Giardia, which sample is a volume of water potentially containing such organisms.

The term "monitoring" is used in the sense of checking or examining systematically for the presence or absence of Cryptosporidium and/or Giardia.

The term "detecting the presence or absence" is used in the sense of clinically acceptable standards for the presence or absence of Cryptosporidium and Giardia. These acceptable standards are approximately 100 cysts or oocysts per 100 liters of sample, and more preferably, approximately seven cysts or oocysts per 100 liters of sample (in regards to Giardia)

The method comprises the step of concentrating the sample by a factor of $1\times10^2$ to $1\times10^5$ of the original volume by removing water, to form a retentate. One or more first antibodies are combined with the retentate. The antibodies, under binding conditions, are capable of binding to one or more antigens of at least one of the selected organisms. A retrievable support is dispensed in the retentate. The retrievable support is selected from the group consisting of a first support and a second support. The first support has a ligand capable of binding the antibodies upon imposition of binding conditions. The second support is associated with the first antibody. Binding conditions are imposed on the retentate holding the antibody and retrievable support. In the presence of at least one of the organisms, an organism-antibody-ligand-support complex is formed in the event the first support is selected and an organism-antibody-support complex is formed in the event such second support is selected. The retrievable support is isolated from the retentate and monitored for the presence of the organism.

As used herein, the term "retrievable support" means grains, particles, beads, and fibers capable of being dispersed in an aqueous media and, separated by immobilization, filtering, partitioning, magnetic separation or the like. Such support may be comprised of a composition such as fiberglass, nitrocellulose, silica, iron oxide, latex, rubber and other nonsoluble materials. A preferred retrievable support is a paramagnetic particle. As used herein, the term "associated" means linked by means of chemical bonds, such as covalent ionic or van der Waals. In a sample having a volume of 10 L to 100 L, reduced volume by a factor of $1\times10^2$ to $1\times10^5$. The volume of paramagnetic particles or beads applied to the retentate is preferably 2–250 µL and, more preferably, 75–150 µL. The capture of the organism on the beads or particles effects a further reduction in volume by a factor of $1\times10^1$ to $1\times10^2$.

Preferably, the step of concentrating the sample is performed with a polymeric membrane. A preferred membrane has a molecular weight cutoff of approximately 100–500 kDa. That is, the membrane tends to pass materials smaller than a molecular weight of 100,000 to 500,000 Daltons. This molecular weight cutoff corresponds approximately to a membrane pore size of 0.01–0.05 µm. A preferred molecular weight cutoff is 500,000 Daltons.

Membranes having a molecular weight cutoff less than 100,000 Daltons may be used. However, membranes with a molecular weight cutoff of 10 to 100 kDa may concentrate at sn unacceptably slow rate. Membranes having a pore diameter of greater than 0.05 µm may also be used. However, membranes with a pore diameter of 0.5–2 µm may not retain organism or organisms may enter the pore structure and be trapped, and have a greater tendency to plug or 'blind over'.

Preferably, the step of concentrating the sample uses such membranes in the presence of Taylor vortices. A preferred means for imparting Taylor vortices is with a membrane that is cylindrical or conical. The cylindrical or conical membrane is received in a cylindrical or conical membrane support. The membrane and membrane retaining support are contained in a larger cylindrical or conical vessel having walls. The vessel walls and the membrane define a chamber for containing sample. Sample contacts the membrane with a pressure drop as the membrane and membrane retaining support are rotated with respect to the sample. The rotation of the membrane creates Taylor vortices. A preferred device for generating Taylor vortices is described in U.S. Pat. No. 4,876,013, which patent is incorporated herein by reference.

Preferably, the first antibody exhibits high affinity for one of the organisms. Polyclonal antibodies exhibiting a high affinity for Giardia cysts are generated by sensitizing mice, rats, rabbits, goats or other animals to Giardia antigens. Monoclonal antibodies to Giardia cysts are available under the trade name Hydroflour combo, Meridian Diagnostics, Inc., Cincinnati, Ohio, USA. Monoclonal antibodies exhibiting high affinity for Giardia cysts are described in the following articles:

Sterling, C. R., M. J. Arrowood, M. M. Marshall, and L. D. Stetzenbach. 1987. The detection of Giardia and Cryptosporidium from water sources using monoclonal antibodies, p. 271–279. In Proceedings for the American Water Works Association Water Quality Technology Conference, Baltimore, Md. American Water Works Association, Denver, Colo.

Sterling, C. R., R. M. Kutob, M. J. Gizinski, M. Verastequi, and L. Stetzenbach. 1989. Giardia detection using monoclonal antibodies recognizing determinants of in vitro derived cysts, p. 219–222. In P. Wallis and B. Hammond (ed.), Advances in Giardia research. University of Calgary Press, Calgary, Alberta, Canada.

Similarly, polyclonal antibodies to Cryptosporidium oocysts are generated by sensitizing rats, rabbits, goats or other animals to Cryptosporidium antigens. Monoclonal antibodies to Cryptosporidium oocysts are available under the trade name Hydroflour combo, Meridian Diagnostics, Inc., Cincinnati, Ohio, USA; and from Bradsure Biologicals Market Marlborough. Monoclonal antibodies are described in the following articles:

Sterling, C. R., M. J. Arrowood, M. M. Marshall, and L. D. Stetzenbach. 1987. The detection of Giardia and Cryptosporidium from water sources using monoclonal antibodies, p. 271–279. In Proceedings for the American Water Works Association Water Quality Technology Conference, Baltimore, Md. American Water Works Association, Denver, Colo.

Sterling, C. R., R. M. Kutob, M. J. Gizinski, M. Verastequi, and L. Stetzenbach. 1989. Giardia detection using monoclonal antibodies recognizing determinants of in vitro derived cysts, p. 219–222. In P. Wallis and B. Hammond (ed.), Advances in Giardia research. University of Calgary Press, Calgary, Alberta, Canada.

Sterling, C. R., and M. J. Arrowood. 1986. Detection of Cryptosporidium sp. Infections using a direct immunofluorescent assay. Pediatr. Infect. Dis. 5:S139–S142.

A preferred support is a paramagnetic bead. Paramagnetic beads are suspended in a sample and isolated from other constituents by imposing a magnetic field on the sample. Preferably, the bead has a ligand capable of binding the first antibody, or has the first antibody bound to it, either directly (covalently), or through a linker ligand (antibody or other ligand or combination of ligands that can bind to antibodies).

As used herein, the term "ligand" refers to a member of a biological binding pair which exhibits affinity or binding capacity for another member, referred to commonly as the antiligand or receptor. Antibodies and antigens, biotin and avidin, biotin and strepavidin, and complementary nucleic acid are common biological binding pairs. A preferred ligand is a second antibody capable of binding such monoclonal or polyclonal first antibody having affinity for Giardia cysts or Cryptosporidium oocysts. By way of example, in the event the antibody having affinity for Giardia cysts or Cryptosporidium oocysts is derived from murine, rat, goat or some other specific animal, the support may carry an antibody capable of binding antibodies derived from murine, rat, goat or such other sources.

Preferably, the ligand, or the antibody, or support-ligand-antibody complex can release the cyst or oocyst upon imposition of releasing conditions. One embodiment of the present method features the imposition of releasing conditions to allow the cyst or oocyst to be examined apart from the support. Preferably, the support is retrieved and separated from the oocyst or cyst. The capture and release of the oocyst effects a further reduction in volume, by a factor of $1 \times 10^3 - 1 \times 10^7$ of the original volume. The step of capture comprising $1 \times 10^1 - 1 \times 10^2$ further reduction in volume from the filtration step to a volume of 50–250 ml.

Preferably, Giardia cysts and Cryptosporidium oocysts are released without altering antigenic epitopes. Preferred releasing conditions comprise altering the pH of solutions suspending the support, mild chaotropic agents, or competitive liquids. A pH of 2.3 will allow a first antibody or a second antibody associated with the support to release the cyst or oocyst to which it is bound. The oocysts and cysts are preferably released in a volume of 50–250 mL, and move preferably 75–125 mL after the support has been removed.

The oocysts and cysts released from the support are preferably indirectly fluorescent-antibody labeled and examined under microscope. However, other means of determining the presence of Giardia cysts and Cryptosporidium oocysts may be used. Such other means include, by way of example, without limitation, automated photo detectors responsive to fluorescent-antibody labeled oocysts or cysts, radio-photographic techniques using radiolabels and enzyme-linked antibody detection systems.

One embodiment of the present invention features a kit for performing an assay for detecting the presence or absence of at least one of the organisms selected from the group consisting of Cryptosporidium and Giardia, which organism potentially exists in a sample comprising a volume of water. The kit comprises one or more first antibodies capable of binding one or more antigens of the selected organisms upon imposition of binding conditions. The kit further comprises a retrievable support selected from the group consisting of a first support and a second support. The first support has a ligand capable of binding the antibodies. The second support is directly associated with the first antibody. The kit is for use with means for reducing the volume of the sample by $1 \times 10^2 - 1 \times 10^5$ to form a retentate. Following the formation of a retentate, first antibodies are combined with the retentate, and, in the event the retrievable support is the first support, the retrievable support is combined with the retentate. In the event the retrievable support is the second support, the retrievable support is added with the first antibody. Upon imposition of binding conditions, an organism-antibody ligand-support complex is formed, in the event the retrievable support is the first support, and an organism-antibody-support complex is formed in the event the retrievable support is the second support.

Preferably, the kit further comprises a membrane for forming a retentate. A preferred membrane is capable of filtration in the presence of Taylor vortices. Preferably, the membrane has a molecular weight cutoff of 100,000–500,000 Da. This molecular weight cutoff corresponds approximately with and a pore size of 0.01–0.05 $\mu$m.

Preferably, the kit comprises means for imposing releasing conditions, such as buffers, chaotropic agents and the like.

Preferably, the kit comprises means for indirectly fluorescently labeling Giardia cysts and Cryptosporidium oocysts to allow examination under microscope.

Surprisingly, and unexpectedly, embodiments of the present invention are capable of recovering approximately 50–70% of Cryptosporidium oocysts present in samples. Samples may range in size from 10–500 L of water and be of vastly different quality. These high levels of recovery are not attained with methods employing cartridge filters. Methods employing cartridge filters have a low efficiency of detection of cysts and oocysts, typically <10%.

These and other advantages will be apparent from the drawings and the detailed description which follows.

DETAILED DESCRIPTION OF THE INVENTION

Figure 1:
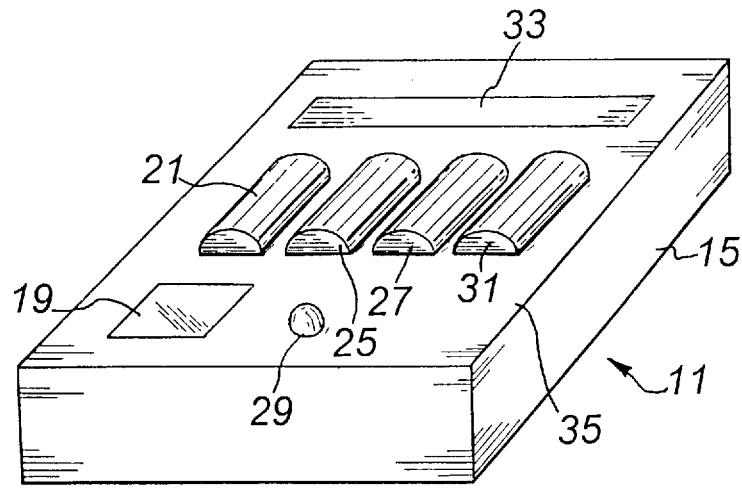
FIG. 1 depicts a kit embodying features of the present invention.

The present invention is directed to methods of detecting Giardia cysts and Cryptosporidium oocysts and articles of manufacture to perform such methods. The methods and articles of manufacture are described with respect to membranes which use Taylor vortices as a preferred embodiment. However, other means of concentrating a sample which do not cause disruption of the cyst or oocyst and have similar efficiencies can be substituted for methods and apparatus which utilize Taylor vortices.

The present invention will be described with respect to a kit, generally designated by the numeral 11. Kit 11 has the following major elements: package 15, membrane 19, antibody composition vial 21, support vial 25, releasing buffer vial 27, magnet 29, immunofluorescent reagent vial 31, and instructions 33.

Package 15 is a box or other suitable means for holding membrane 19, antibody composition vial 21, support vial 25, releasing buffer vial 27, magnet 29 immunofluorescent reagent vial 31 and instructions. Package 15 may take many different forms and shapes. As depicted in FIG. 1, Package 15 is a rectangular box with an expanded foam insert 35 to cushion and insulate the vials contained therein.

Membrane 19 is preferably comprised of hydrophillic polymeric composition. The membrane has pores with a molecular weight cutoff of 100,000–500,000 Da and most preferably, about 500,000 Da. This molecular weight cut off corresponds approximately to a pore size of 0.01–0.05 $\mu$m.

Membrane 19 is capable of assuming a cylindrical shape. Preferably, membrane 19 is capable of being received in a vortex flow filtration assembly, generally described in FIG. 2. A detailed description of vortex flow assemblies is provided in U.S. Pat. No. 4,876,013 to Schmidt et al., which reference is incorporated herein.

Figure 2:
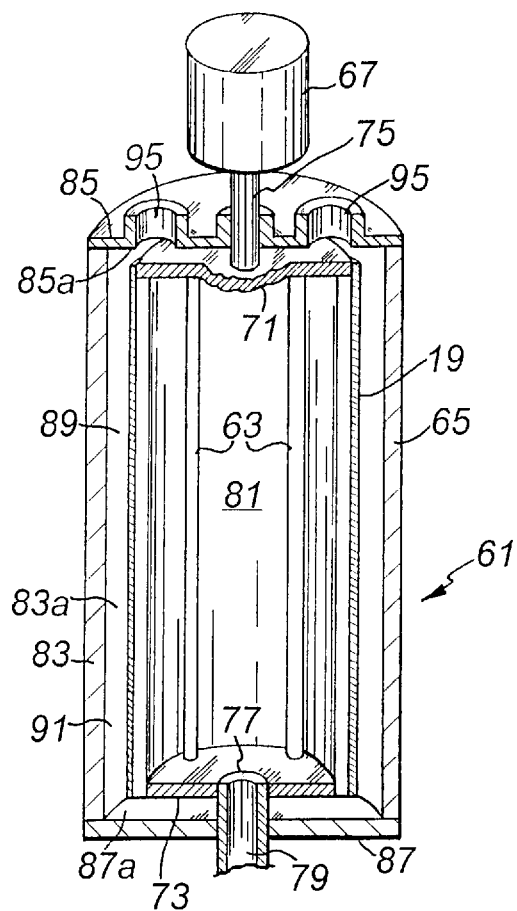
FIG. 2 depicts a vortex flow membrane device.

Turning now to FIG. 2, a vortex flow assembly generally designated by the numeral 61 comprises the following major elements: a membrane support 63, a stationary vessel 65, and motor 67. Membrane 19 is held on rotatable membrane support 63.

Membrane 19 may be cylindrical or may be a sheet of porous polymeric material which can be rolled and secured by suitable clips adhesive or welds (not shown) in the shape of a cylinder surrounding the membrane support 63. Membrane support 63 has a top end 71 and a bottom end 73. Top end 71 is mechanically linked to motor 67 by a shaft 75.

Bottom end 73 has an axial opening 77 which rotatably receives a hollow shaft 79.

Membrane 19 and membrane support 63 define an inner chamber 81 for receiving fluids drawn or compelled through membrane 19. Fluid in inner chamber 81 is removed by hollow shaft 79.

Stationary vessel 65 has the following major elements: a cylinder housing 83, a top housing 85, and a bottom housing 87. Cylinder housing 83 has cylindrical walls 83a defining an open cylinder having a top and a bottom. Top housing 85 is received at the top of cylindrical housing 83. Bottom housing 87 is received at the bottom of the cylinder housing 83. Bottom housing 87 and top housing 85 have substantially planar surfaces 87a and 85a, respectively, which with cylindrical walls 83a define a cylinder chamber 89. Cylinder chamber 89 is capable of receiving membrane 19 and membrane support 63. The area 91 between cylindrical wall 83 and membrane 19 of stationary chamber 89 is for receiving sample.

Top housing 85 has an opening 95 in communication with area 91 for receiving sample and an opening 97 for supplying pressure, if desired. Top housing 85 rotatably receives shaft 75.

Bottom housing 87 receives hollow shaft 79 to allow inner chamber 81 to be placed in fluid communication with a vacuum source or to drain inner chamber 81.

Preferably bottom housing 87 and/or top housing 85 are removable from cylinder housing 83 to allow servicing of the membrane.

Sample is received in area 91 of cylinder chamber 89. As membrane 19 is rotated on shaft 75 by motor 67, Taylor vortexes are generated in area 91 which sweep the membrane and prevent occlusion. Retentate is maintained in area 91. Filtrate enters inner chamber 81 and is removed via hollow shaft 79. Samples are reduced in volume by $1\times10^2$ to $1\times10^5$ using the vortex flow assembly 61.

Returning now to FIG. 1, antibody composition vial 21 contains first antibodies to one or more of the organisms selected from the group of Giardia cysts and Cryptosporidium oocysts. The antibody composition contained in vial 21 may further comprise buffers, salts, surfactants, and bulking proteins known in the art. The antibody composition held in vial 21 may be a solution or a lyophilized powder. In the event the first antibody composition held in vial 21 is a lyophylized powder, the kit may comprise further vials (not shown) containing appropriate diluents and solutions for reconstitution.

The antibody composition of vial 21 is capable of binding to an antigen carried or Giardia cysts or Cryptosporidium oocysts to form a organism-antibody complex. The antibody composition of vial 21 is added to the retentate formed with membrane 19.

Support vial 25 contains a retrievable support and, most preferably, paramagnetic beads. Preferably, the paramagnetic bead are single domain magnets and are super paramagnetic exhibiting no residual magnetism. The particles or beads may be comprised of magnet-type particles, although they can also be other magnetic metal or metal oxides, whether in impure, alloy, or composite form, as long as they have a reactive surface and exhibit an ability to react to a magnetic field. Other materials that may be used individually or in combination with iron include, but are not limited to, cobalt, nickel, and silicon. Methods of making magnetite or metal oxide particles are disclosed in Vandenberghe et al., "Preparation and Magnetic Properties of Ultra-Fine Cobalt Ferrites," *J. Of Magnetism and Magnetic Materials.*

15–18:1117–18 (1980): E. Matijevic, "Mono Dispersed Metal (Hydrous) Oxide—A Fascinating Field of Colloidal Science," *Acc. Chem. Res.*, 14:22–29 (1981) the disclosures of which are incorporated herein by reference. A magnetic bead suitable for application to the present invention includes a magnetic bead containing carboxyl functional groups marketed under the trade name Bangs Laboratories, Inc. (Indiana, USA). A preferred bead is approximately 50 nm to 5 μm in diameter.

The retrievable support contained in support vial 25 comprises a ligand capable of binding to the antibody-organism complex. A preferred ligand is a second antibody. The second antibody is chosen to bind specifically with the first antibody. Upon binding, an organism-antibody-ligand-support complex is formed.

Magnet 29 is capable of immobilizing retrievable supports upon the inside wall of a vessel, such as laboratory cuvette or test tube by pressing the magnet 29 on the outside wall. The paramagnetic particles agglomerate on the side of the vessel or tube adjacent to the magnet 29. Excess retentate can be removed and the organism-antibody-ligand-support complexes resuspended. A typical volume of magnetic beads is 25–250 μL and, most preferably, 50–125 μL of beads.

Releasing buffer vial 27 contains chaotropic agents, such as basic buffers which release the organism from the support. After the organism-antibody-ligand-support-complex has been isolated from the retentate, the complex is resuspended in releasing buffer and the support isolated with the use of magnet 29. The resuspended organisms occupy a fluid volume of 50–100 μL.

Immunofluorescence reagent vial 31 contains immunofluorescent reagent to indirectly label the organism. Additional reagents (not shown) may be required to return the pH to a substantially neutral level. Immunofluorescent reagent, if comprised of a plurality of components, may be contained in additional vials (not shown). The organism, released from the support, is combined with the immunofluorescent reagent to label the organism. The organism can be detected through microscopic examination or by other means.

Instructions 33 describes the methods and procedures to detect Giardia cysts and Crytosporidium oocysts. The instructions are summarized in the following discussion of the operation of the assay.

In operation, membrane 19 is removed from kit 11 and placed upon a membrane support 63. The membrane is comprised of a hydrophillic polymer of 500,000 Da molecular weight cut off, corresponding to a 0.05 micrometer pore size. The membrane has a transmembrane flux rate of approximately 40 to 115 millimeters per minute. Membrane support 63 and membrane 19 are placed within cylindrical housing 83. Membrane support 63 is mechanically linked to motor 67 by shaft 75. The top housing 83 and bottom housing 87 are affixed to the end of cylindrical cylinder housing 83.

A sample of approximately 10–500 L is received through opening 95 and into the area 91 between cylindrical wall 83 and membrane 19. A small pressure of 0–15 psi is exerted in the area 91 by the incoming sample and additional pressure can be asserted through opening 97 if desired.

As membrane 19 is rotated on shaft 75 by motor 67, Taylor vortexes are generated which sweep the membrane 19 and prevent occlusion. The membrane rotational speed is approximately 2,000 to 4,000 revolutions per minute.

The filtrate enters inner chamber 81 and is removed via hollow shaft 79. A negative pressure of minus 5 to minus 12 pounds per square inch is exerted through the shaft opening 75.

The retentate is removed from area 91 by pouring such retentate from opening 95 or removing the top housing 83. The retentate constitutes 5 to 250 ml of an original 10 to 500 L sample, a reduction in volume of $1 \times 10^2$ to $1 \times 10^5$.

The retentate, having a volume of approximately 5 to 15 ml is separated from the membrane 19 and the vortex flow assembly 61 by pouring such retentate from opening 95 or removing the top housing 83. The retentate is placed in a suitable containment vessel such as a test tube. Antibody composition, contained in vial 21, is placed in the retentate and incubated with gentle mixing for 10 to 60 minutes. The antibody composition of vial 21 comprises one or more antibodies capable of binding to an antigen carried on Giardia or Crytospordium oocyst. In the presence of a Crytospordium oocyst or Giardia cyst the antibody forms an organism-antibody complex.

Paramagnetic beads, contained in support vial 25, having a volume of approximately 25–250 μL and, most preferably, 75–125 μL, are combined with the retentate. These paramagnetic beads are conjugated with antipolyclonal or antimoniclonal antibody. That is, the ligand of the beads is capable of forming a complex with the first antibody of the first antibody composition.

The paramagnetic beads are incubated in the retentate, with gentle mixing, from 10 to 60 minutes. In the presence of a Cryptosporidium oocyst or Giardia cyst an organism-antibody-ligand-support complex is formed. Magnet 29 is placed against the test tube to immobilize the paramagnetic beads along the inside wall of the vessel adjacent to the magnet.

The retentate can be combined with further beads and the process repeated 1 to 3 times to insure full recovery of cysts and oocysts. The beads, which have been isolated from the retentate, are combined and placed in a 50–200 μL releasing buffer and, more preferably, 75–125 μL of releasing buffer, held in releasing buffer vial 27. Releasing buffer contains chaotropic agents such as basic buffers which release the organism from the support. A preferred releasing buffer has a pH of 2 to 3. Preferably, the chaotropic agents does not destroy the antigenic epitopes of the oocysts or cysts.

After removal of the cyst or oocysts from the beads, the beads are separated by immobilizing the beads along the side of the test tube containing the releasing buffer and beads. The releasing buffer is separated from the beads and the pH adjusted to a neutral pH. The organisms are resuspended in a solution of 50–200 μL of water and, more preferably, 75–125 μL of water. Immunofluorescent reagents comprising a labeled antigen capable for forming a complex with the cysts or oocysts are removed from immunofluorescent reagent vial 31 and combined with the neutralized sample. The immunofluorescent reagents are allowed to incubate from 10 to 60 minutes. The cysts or oocysts, if present, are available for examination under microscope.

The organisms may be detected by DNA and RNA analysis. Suitable probes would be isolated from genomic DNA, messenger RNA and/or ribosomal RNA. Techniques for performing polymerase chain reaction (PCR) analysis and nucleic acid hybridization analysis are known in the art.

The present method and articles of manufacture provide for reliable, and cost effective detection of Giardia cysts and Cryptosporidium oocysts. These and other advantages will be further described with respect to the following examples.

EXAMPLE 1

The following example features the isolation and examination of Cryptosporidium oocysts. The isolation and examination of Giardia cysts would be similar, however, antibody compositions for Giardia cysts would be substituted for antibodies for Cryptosporidium oocysts.

Polyclonal antibodies directed to Cryptosporidium oocyst antigens were developed in rabbits. Other animals may be substituted for rabbits. The choice being determined to some degree by the familiarity of the researcher or individual skilled in the art with a particular animal, availability of the animal, and its cost of upkeep.

Oocysts were purified and formalin fixed with 10% formalin. Approximately $1-5 \times 10^6$ oocysts were administered subcutaneously in the presence of Freund's adjuvant. Antibodies are isolated from ascites and serum from the rabbits by affinity chromatography. Polyclonal antibodies could also be developed using a purified extract of oocysts comprising antigenic compositions derived from the oocyst wall.

Polyclonal antibodies directed to Giardia cyst antibodies would be prepared in rabbits or other animals in a similar manner. That is, Giardia cysts would be purified and formalin fixed with 10% formalin. Approximately $1-5 \times 10^6$ cysts would be administered subcutaneously in the presence of Freund's adjuvant to a rabbit or desired animal. Antibodies would be isolated from ascites and serum from such rabbit or other immunized animal by affinity chromatography.

As with Cryptosporidium directed polyclonal antibodies, polyclonal antibodies could be developed using a purified extract of Giardia cysts comprising antigenic compositions derived from the cyst wall.

Monoclonal antibodies directed to Cryptosporidium oocysts or Giardia cysts would be developed in the following manner. Bab/CJ mice would be immunized intraperitoneally, with oocysts or cysts which have been purified and formalin fixed in 10% formalin. The immunization is repeated several times. Four to six days after the final immunization the animals are sacrificed. The spleen is aseptically removed and placed in a petri dish with 5 ml cell culture media. The spleens are rinsed in sterile media then transferred to a new petri dish containing 5 ml media. The spleen cells are screened using sterile forceps and 60/80 mesh stainless steel screen.

The disrupted cells are transferred to a conical vessel and allowed to settle. The supernatant is poured off and the remaining cells and liquid are centrifuged (400×g) for fifteen minutes. The cells are resuspended in 0.5 ml fetal calf serum (FCS). To the resuspended cells, 4.5 ml red blood cell lysis buffer (10 $\mu$M Tris pH 7.2, 144 $\mu$M NH$_4$Cl) is added. The resuspended cells are allowed to incubate in red blood cell lysis buffer for five minutes. After incubation, 10 ml of cold media with media with FCS (2.5%) is added to the resuspended cells. The cells are again spun at 400×g for five minutes. The cells are then resuspended in 25 ml media.

Myeloma cells are prepared with SP2/0cells (ATCC, Rockville, Md.). These cells are thawed, grow in cell culture media and prepared at a concentration of $1 \times 10^7$ cells per ml.

Splenocytes and myeloma cells are combined in a ratio of three splenocytes cells to one myeloma cell. The mixture of cells is spun at 400×g for five minutes and the cells resuspended in 25 ml of media no serum. The resuspended cells are spun at 400×g for ten minutes and the supernatant removed.

The pellet is tapped to resuspend and the test tube containing the pellet is placed in a water bath of 37° C. To the pellet 1 ml of 50% polyethyleneglycol (PEG 1,500–3,000 mw)/media at 37° C. is added dropwise over one minute ($\approx$1 drop every 3 sec.). This mixture is gently stirred with the pipette tip during and for up to one minute after the addition.

Next, 1 ml of media/no serum at 37° C. is added over a one minute period with stirring. This step is repeated, and followed with the addition of 2 ml DME/no serum at 37° C. over a one minute period. Next, 7 ml of media/2.5% FCS at 37° C. is added over 2 minutes while swirling the tube, to dilute out the PEG.

This mixture is spun, at 400×g for 5 minutes, and the supernatant is aspirated.

The cells are then resuspended in 10 ml of media/10% FCS medium at 37° C. by shooting media at the pellet and stirring. The concentration of the cell mixture is adjusted to approximately $1 \times 10^7$ cells per ml by gently swirling the cells in the tube.

These cells are plated in 96 well tissue culture dishes at $1 \times 10^6$ cells per well. Cells are maintained with the addition of 0.1 ml 1×hypoxanthine/aminopterine/thymidine (HAT) to each well the day following plating. On the fifth, seventh and ninth day following plating, 0.1 ml of fluid is removed from each well and replaced with 0.1 ml×HAT. This process is repeated every 3–4 days thereafter. After 1–3 weeks hybrid cells are observed as small clusters. Hybridomas secreting antibodies of the desired specificity are detected by performing indirect immunofluorescence microscopy using the hybridomas supernatants.

Antibodies are isolated by affinity chromatography. Antibodies from the clusters are tested for specificity to Giardia or Cryptosporidium antigens. Clones generating desired antibodies are expanded and cultured.

Antibodies capable of binding polyclonal antibodies derived from rabbit were obtained from Sigma Chemical catalog no. R-2004 (St. Louis, Mo., USA) and Jackson Immunoresearch Laboratories, Inc., West Grove, Pa., (Affinipure Goat antiRabbit IgG+L), catalog no. 111-005-003. Antibodies capable of binding monoclonal or polyclonal antibodies derived from other animals are readily available.

Antibodies are applied to beads by a carbodiimide coupling reaction. See: Hoare, P. G. and Koshland, D. E. (1967) J.BC 242:2447–2453 and Beuver, E. C. et al., (1985) "The Pathogenic Neisseria," ASM Press, Washington, D.C. The beads comprise 67% magnetite and have polystyrene/divinylbenzene/carboxylic acid composition groups, and a size of f 0.8 $\mu$m diameter. These beads are available from Bangs Laboratories, Carmel, Ind. (USA), catalog no. M008002CN.

The coupling of antibodies to beads is performed by dialysing beads against deionized water at pH 5.0. In a reaction tube, 100 $\mu$L of beads (10 mg) and 0.5 ml of water are combined. The beads are immobilized magnetically after 30 minutes and the supernatant is aspirated. A further 0.1 ml of distilled water is adjusted to pH 5.0 with HCl is added to the beads. Next, 0.5 ml of 1-ethyl-3-diamethylaminopropylcarbodiimide (CDl) solution is added to the beads. The solution comprises 20 mg CDl/ml deionized H$_2$O (pH 5.0). Approximately 0.5 ml of antibody solution containing 2 mg antibody/ml in deionized water (pH 5.0).

This solution is mixed by rotation of the reaction tube end over end at room temperature. During the first hour, the pH is maintained at 5.0 by the addition of small amounts of dilute NaOH. The solution is mixed over an 8–12 hour period at 4° C.

The beads are separated from the supernatant and resuspended in 1 ml of 0.5M NaCl in phosphate buffer (PBS). The beads are immobilized, the supernatant removed and resuspended in 2 m PBS, 0.5% bovine serum albumin (BSA). The beads are mixed again by end over end rotation at room temperature for one hour. The beads are again immobilized, the supernatant aspirated, and the beads resuspended in 1 ml PBS/BSA/0.02 sodiumazide. The beads are stored at 4° C. until used.

Water samples of 10 to 100 liters of water quality of 1 to 30 ntu, were concentrated using a vortex flow assembly (Membrex, Inc., Garfield, N.J., USA). A hydrophillic, polymeric membrane of 500,000 Da molecular weight cutoff of approximately 0.05 micrometer pore size (Membrex, Inc., of Garfield, N.J., USA), was used at a rotational speed of 2,000 to 4,000 rpms. The system configuration provided 0 to 15 pounds per square inch of pressure from a water source with a permeate negative pressure of minus 5 to 12 pounds per square inch. In this configuration the membrane exhibited a membrane flux rate of 40 to 150 millimeters per minute. The 10 to 500 liter samples were processed and the retentate removed when the volume approached 5 to 15 ml.

The retentate was placed in a test tube. A Crytosporidium specific polyclonal antibody was added to the retentate and allowed to incubate with gentle mixing for 10 to 60 minutes. The antibody is combined with the retentate to provide an excess of antibody. Typically, 16 µg of antibody provides a 2,000 fold excess for labeling 100 oocysts. The antibody formed a Cryptosporidium oocyst-antibody complex.

Following incubation, paramagnetic beads (Bangs Laboratories, Carmel, Ind., USA) having a range of diameters from 50 nm to 2 µm were added to the retentate. The beads carried a ligand, comprising a second antibody as previously described. This second antibody was capable of binding the first antibody after incubation with gentle mixing for 10 to 60 minutes, the paramagnetic beads were immobilized along the side of the test tube containing the retentate. In the presence of Cryptosporidium oocysts, the beads formed an oocyst -antibody-ligand-support complex.

The retentate was poured into a separate test tube and additional beads added. The process of incubating the magnetic beads, immobilizing the magnetic beads and pouring the retentate into a separate vial was performed 1 to 3 times to insure the oocysts were removed from the solution.

The magnetic beads are combined with a releasing solution comprising a solution of 0.1 m glycine/hydrochloride of pH 2–3. The oocysts were released into the solution. The beads immobilized with a magnet and releasing solution containing the released oocysts was poured from the test tube with magnet. The releasing solution was adjusted to a pH of 6–8.

Fluorescent labeled antibodies MeriFlour Combo (catalog no.250050, Meridian Diagnostics, Cincinnati, Ohio, USA), or primary antibody such as Hydroflour Combo (catalog no. 70800, Ensys Research, Triangle Park, N.C., USA), followed by labeling reagent such as fluoroescein conjugates $I_g$MAb (catalog no. 315-015-020) specific for the oocysts and cysts were added to the test tube and allowed to incubate for 10 to 60 minutes. The oocysts and cysts were then examined by microscope.

Embodiments of the present invention resulted in consistently high recovery of oocysts from samples. The recoveries of oocysts were approximately 70 percent. The combination of vortex flow filtration and magnetic particle separation achieved a $1\times10^2$ to $1\times10^6$ concentration of environmental examples with overall Crytosporidium oocysts recovery efficiencies of greater than 50 percent. By comparison the ASTM detection method using cartridge filter contentration exhibits a dramatically lower recovery rate.

Thus, the present invention provides practical means for the detection of Crytosporidium oocysts and Giardia cysts.

While preferred embodiments have been illustrated and described, it is understood that the present invention is capable of variation and modification and, therefore, should not be limited to the precise details set forth but should include such changes and alterations that are within the purview of the following claims.

We claim:

1. A method for detecting Cryptosporidium oocysts in a water sample, comprising:

a) providing a water sample having an initial volume and an initial number of Cryptosporidium oocysts;

b) providing a capture reagent comprising a retrievable solid support linked to an antibody, wherein the antibody binds specifically to Cryptosporidium oocysts;

c) concentrating the initial volume of the water sample by vortex flow filtration to form a retentate solution;

d) forming an incubation mixture comprising the capture reagent of step b) in the retentate solution of step c);

e) incubating the incubation mixture of step d) under conditions appropriate for the binding of the capture reagent to Cryptosporidium oocysts present in the retentate;

f) separating Cryptosporidium oocysts bound to the capture reagent from other components of the incubation of step b); and g) detecting Cryptosporidium oocysts separated in step f), steps a)–f) combining to yield a resolution sufficient to detect greater than 50% of the initial number of Cryptosporidium oocysts present in the water sample.

2. The method of claim 1 wherein the retrievable support is a grain, particle, bead or fiber characterized by the ability to be dispersed in an aqueous solution and being recoverable by a method selected from the group consisting of immobilization, filtering, partitioning and magnetic separation.

3. The method of claim 2 wherein the retrievable support is a paramagnetic bead.

4. The method of claim 2 wherein the retrievable support is selected from the group consisting of fiberglass, nitrocellulose, silica, iron oxide, latex and rubber.

5. The method of claim 1 wherein the antibody is monoclonal.

6. The method of claim 1 wherein the antibody is polyclonal.

7. The method of claim 1 wherein detection is by immunofluorescence.

8. A method for detecting Cryptosporidium oocysts in a water sample, comprising:

a) providing a water sample having an initial volume and an initial number of Cryptosporidium oocysts;

b) providing a first antibody, wherein the first antibody binds specifically to Cryptosporidium oocysts;

c) providing a capture reagent comprising a retrievable solid support linked to a second antibody, wherein the second antibody binds specifically to the first antibody;

d) concentrating the initial volume of the water sample by vortex flow filtration to form a retentate solution;

e) forming an incubation mixture comprising the first antibody of step b) and the capture reagent of step c) in the retentate solution of step d);

f) incubating the incubation mixture of step e) under conditions appropriate for the binding of the first antibody to Cryptosporidium oocysts present in the retentate, and for the binding of the capture reagent to the first antibody; and g) separating a complex comprising one or more Cryptosporidium oocysts bound specifically to a first antibody and a capture reagent from other components of the incubation mixture of step f); and h) detecting Cryptosporidium oocysts separated in step g), steps a)–h) combining to yield a resolution sufficient to detect greater than 50% of the initial number of Cryptosporidium oocysts present in the water sample.

9. The method of claim 8 wherein the retrievable support is a grain, particle, bead or fiber characterized by the ability to be dispersed in an aqueous solution and being recoverable by a method selected from the group consisting of immobilization, filtering, partitioning and magnetic separation.

10. The method of claim 9 wherein the retrievable support is a paramagnetic bead.

11. The method of claim 9 wherein the retrievable support is selected from the group consisting of fiberglass, nitrocellulose, silica, iron oxide, latex and rubber.

12. The method of claim 8 wherein the first antibody is monoclonal.

13. The method of claim 8 wherein the first antibody is polyclonal.

14. The method of claim 8 wherein the second antibody is monoclonal.

15. The method of claim 8 wherein the second antibody is polyclonal.

16. The method of claim 8 wherein detection is by immunofluorescence.

* * * * *